US00PP32619P2

(12) United States Plant Patent
Warren

(10) Patent No.: US PP32,619 P2
(45) Date of Patent: Dec. 15, 2020

(54) CHERRY TREE NAMED 'JFS KW21PS'

(50) Latin Name: *Prunus sargentii*
Varietal Denomination: JFS KW21PS

(71) Applicant: J. Frank Schmidt & Son Co., Boring, OR (US)

(72) Inventor: Keith S. Warren, Gresham, OR (US)

(73) Assignee: J. Frank Schmidt & Son Co., Boring, OR (US)

( * ) Notice: Subject to any disclaimer, the term of this patent is extended or adjusted under 35 U.S.C. 154(b) by 0 days.

(21) Appl. No.: 16/873,406

(22) Filed: Apr. 8, 2020

(51) Int. Cl.
*A01H 5/08* (2018.01)
*A01H 6/74* (2018.01)

(52) U.S. Cl.
USPC ..... Plt./182

(58) Field of Classification Search
USPC ..... Plt./156, 181, 182
See application file for complete search history.

(56) References Cited

PUBLICATIONS

Declaration of Keith S. Warren Under 37 CF.R. § 1.132 dated Apr. 23, 2020.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A variety of ornamental cherry that combines a strongly upright branch habit, a narrow form, and deep pink flowers.

7 Drawing Sheets

Latin name of the genus and species of the plant claimed and variety denomination: *Prunus sargentii* 'JFS KW21PS'.

BACKGROUND

In 1989, I began a program to select improved cultivars of *Prunus sargentii* as ornamental cherry trees. In May of 1989, I planted 264 open pollinated seedlings of *Prunus sargentii* in a nursery row in Boring, Oreg. As these seedling trees grew, I marked and selected those with the best foliage and form, and in the March 1992, I selected and numbered the best 24 trees to be transplanted to wider spacing in the same nursery and destroyed the remaining trees. Of these trees, the one that I numbered as '03' proved to have an excellent characteristics of a broadly vase shaped form, bright fall color, and late foliage emergence, but its flowers were only typical of the species. I chose not to introduce '03', but instead, I collected its open pollinated seed in the fall of 2002 to grow for future selection. Of the other 23 transplanted trees, I destroyed 22 and eventually introduced one as the cultivar 'JFS-KW58,' not patented.

In the fall of 2002, I planted the open pollinated seed of '03' into a bed in a Boring, Oreg. nursery, then grew the seedlings for two seasons. In the March 2005, I transplanted the 24 small trees grown from '03' seed and grew them in a Boring, Oreg. nursery for four seasons, marking and recording their characteristics. In the fall of 2008, I decided that only one tree was of high enough quality to warrant potential introduction, so I destroyed the other 23. I was first attracted to this particular tree because of its flowers which were large and brighter and deeper pink than any other *Prunus sargentii* seedling that I had seen. In February of 2010, I named this tree 'JFS KW21PS' and transplanted it to wider spacing for further evaluation.

In 2014, 2015, 2016, and 2017, I directed test propagation of a total of 35 trees by budding in a Canby, Oreg. nursery and a total of 41 trees by budding in a Boring, Oreg. nursery onto *Prunus avium* rootstock. I also directed test propagation of 65 trees by softwood cutting in 2015. Of these test propagated trees, 25 have been retained for stock increase in a nursery stock block in Boring Oreg. and the rest were destroyed. From all this propagation, I determined that the characteristics of my new variety were firmly fixed and all propagated plants have been identical to my new variety in every way observed.

SUMMARY OF THE INVENTION

This new cultivar possesses a unique combination of characteristics in that it combines prolific production of unusually bright, deep pink flowers with a narrow inverted cone shaped form.

BRIEF DESCRIPTION OF THE DRAWINGS

The colors of an illustration of this type may vary with lighting conditions and, therefore, color characteristics of this new variety should be determined with reference to the observations described herein, rather than from these illustrations alone.

DETAILED BOTANICAL DESCRIPTION

Figure 1:
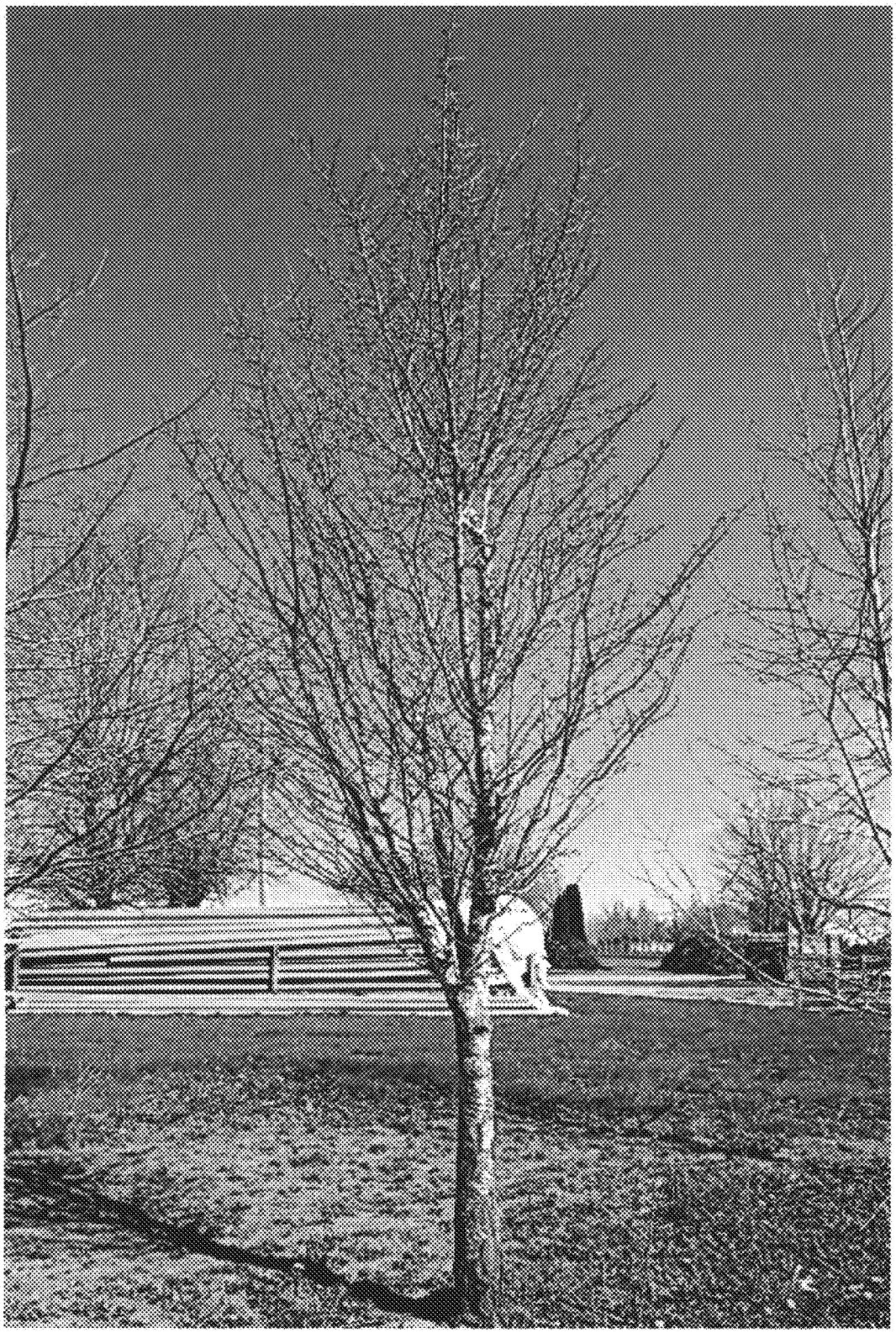
FIG. 1: Shows the upright branch habit and form of a 13 year old tree in winter.
Figure 2:
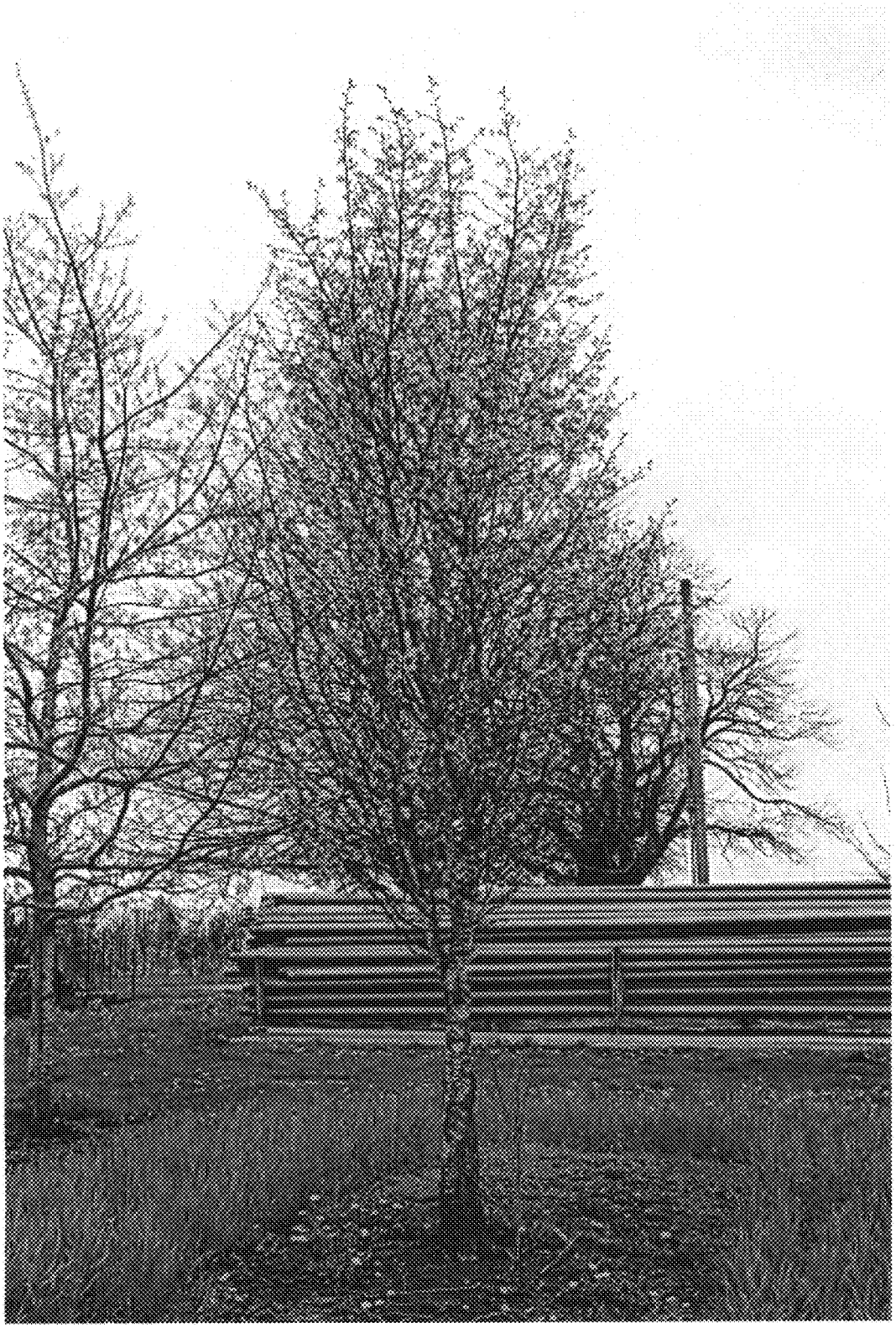
FIG. 2: Shows the form of a 13 year old tree in flower.
Figure 3:
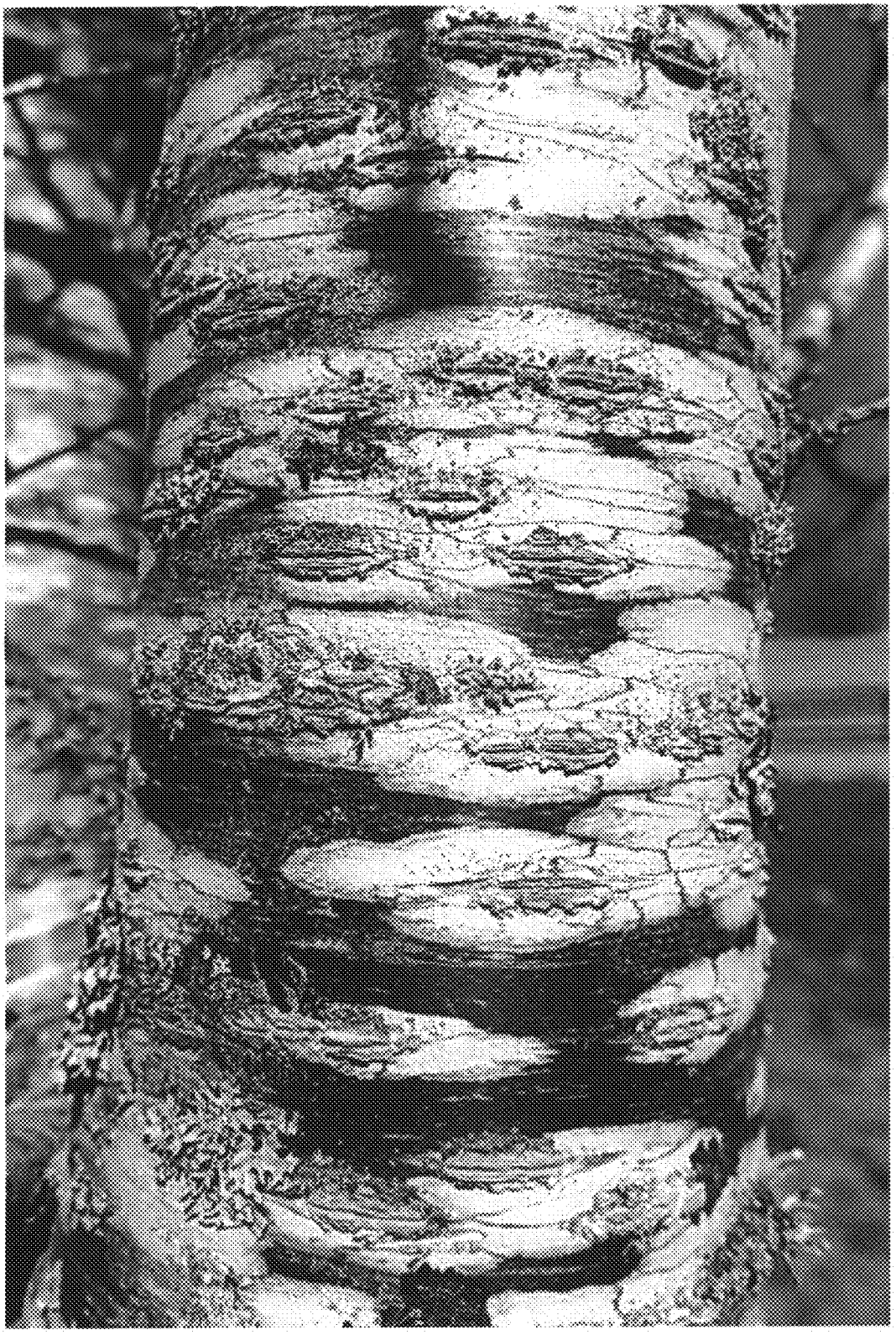
FIG. 3: Shows the mature bark on a 13 year old tree.
Figure 4:
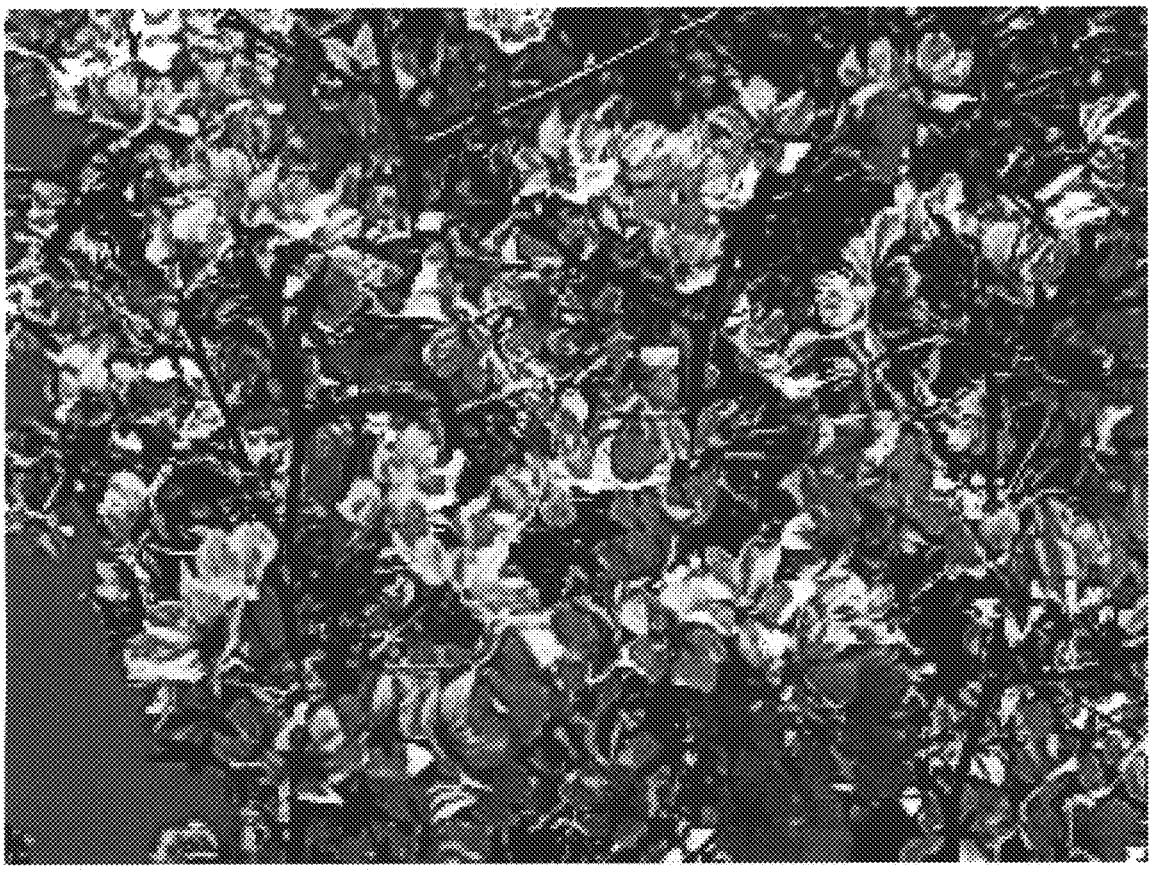
FIG. 4: Shows the prolific flowering of an 8 year old tree.
Figure 5:
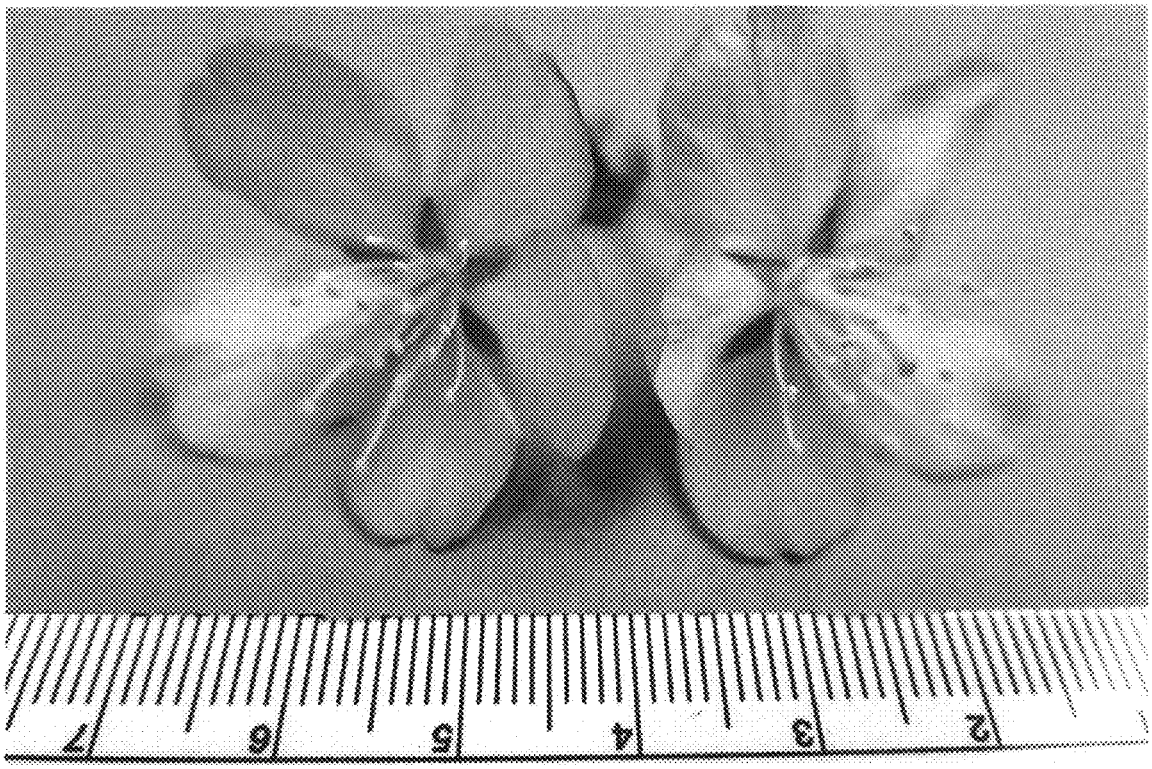
FIG. 5: Shows a close up of the flowers on a display board with scale.
Figure 6:
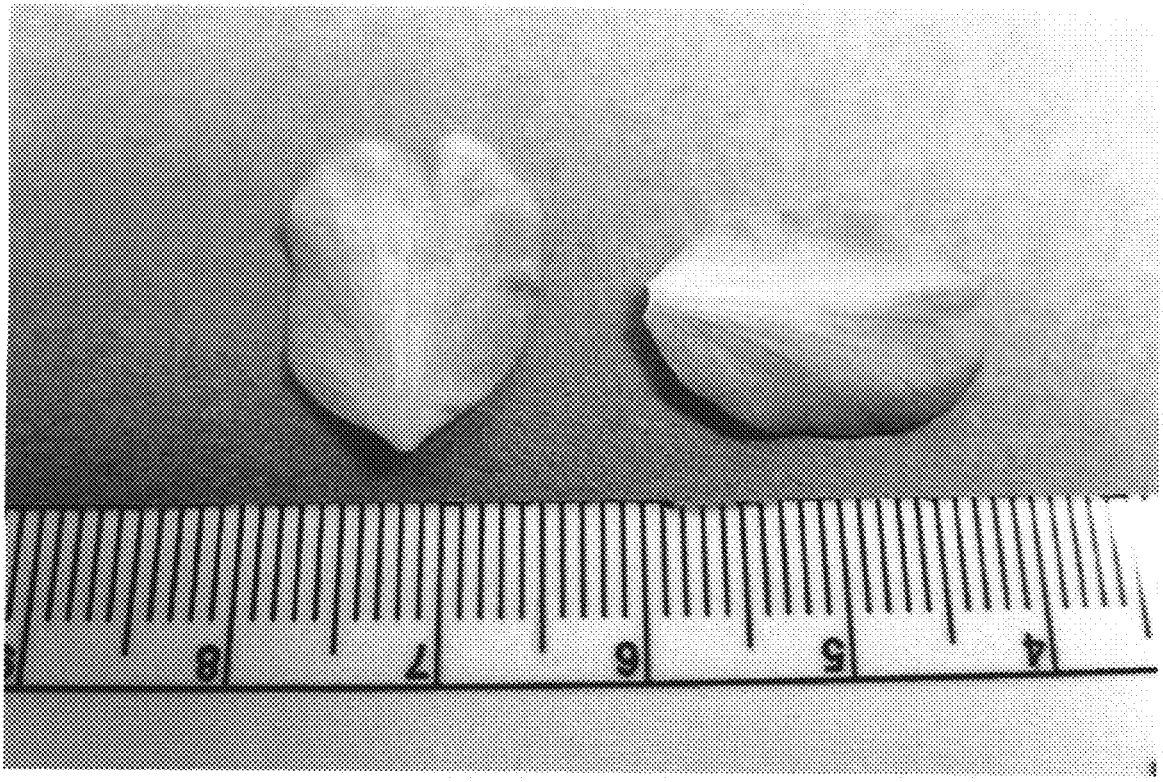
FIG. 6: Shows a close up of two flower petals on display board with scale.
Figure 7:
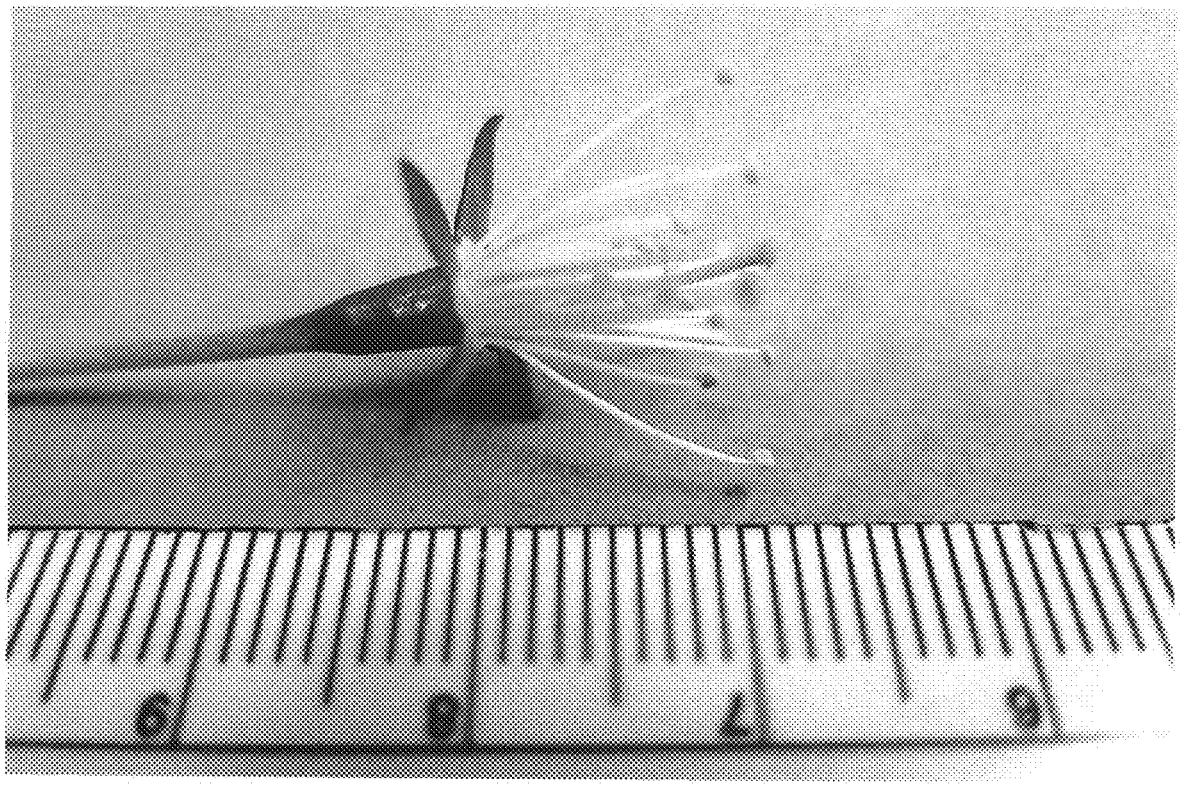
FIG. 7: Shows a close up of the flower with petals removed.
Figure 8:
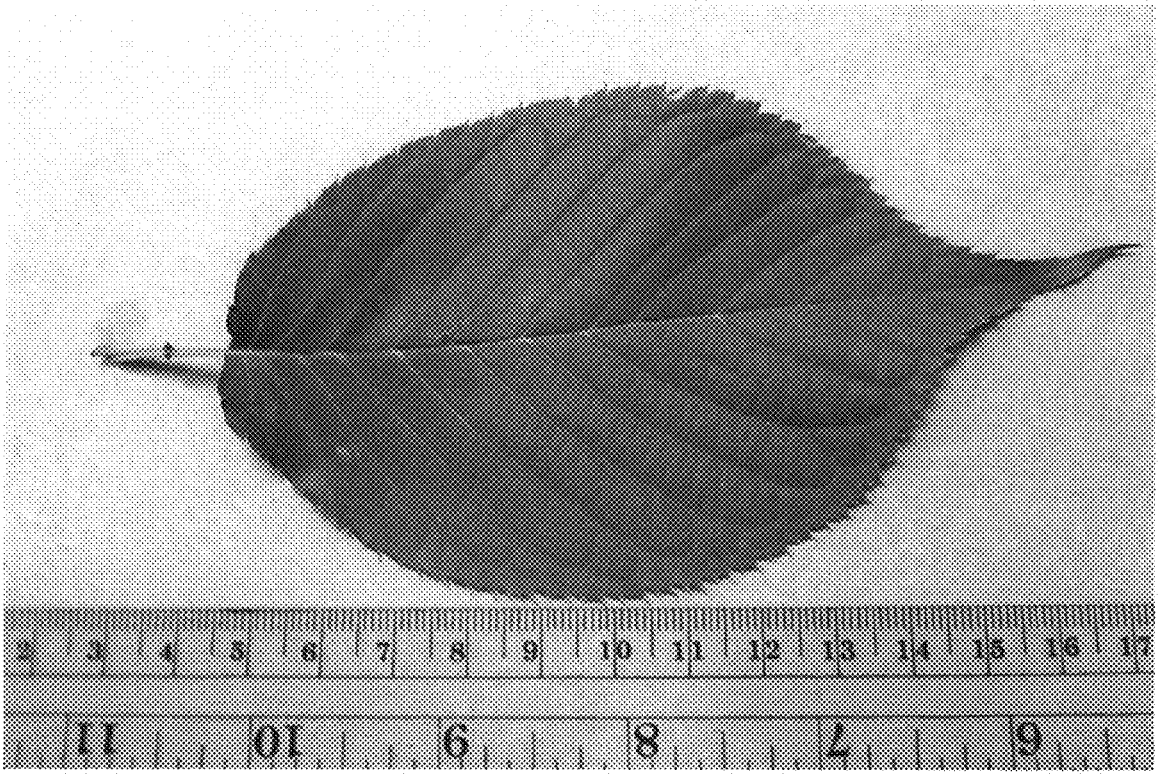
FIG. 8: Shows a single summer leaf on a display board with a scale.
Figure 9:
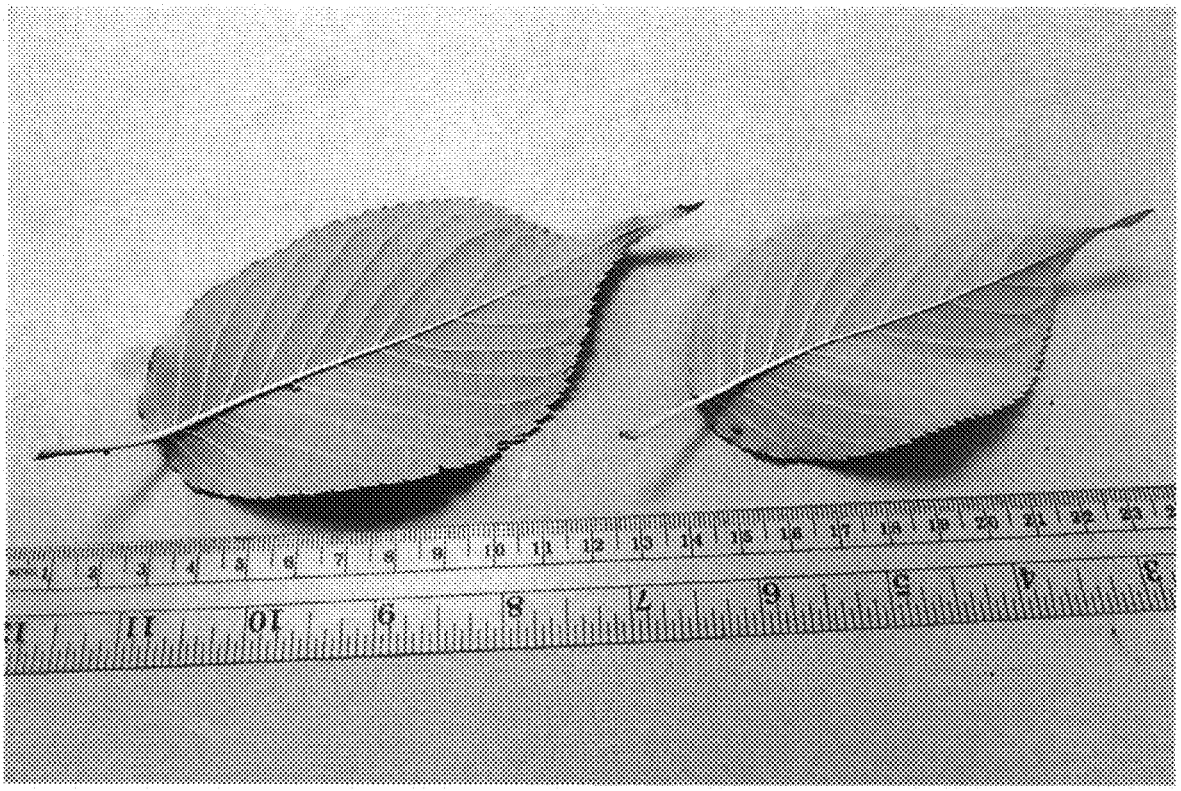
FIG. 9: Shows the underside two summer leaves on a display board with a scale.
Figure 10:
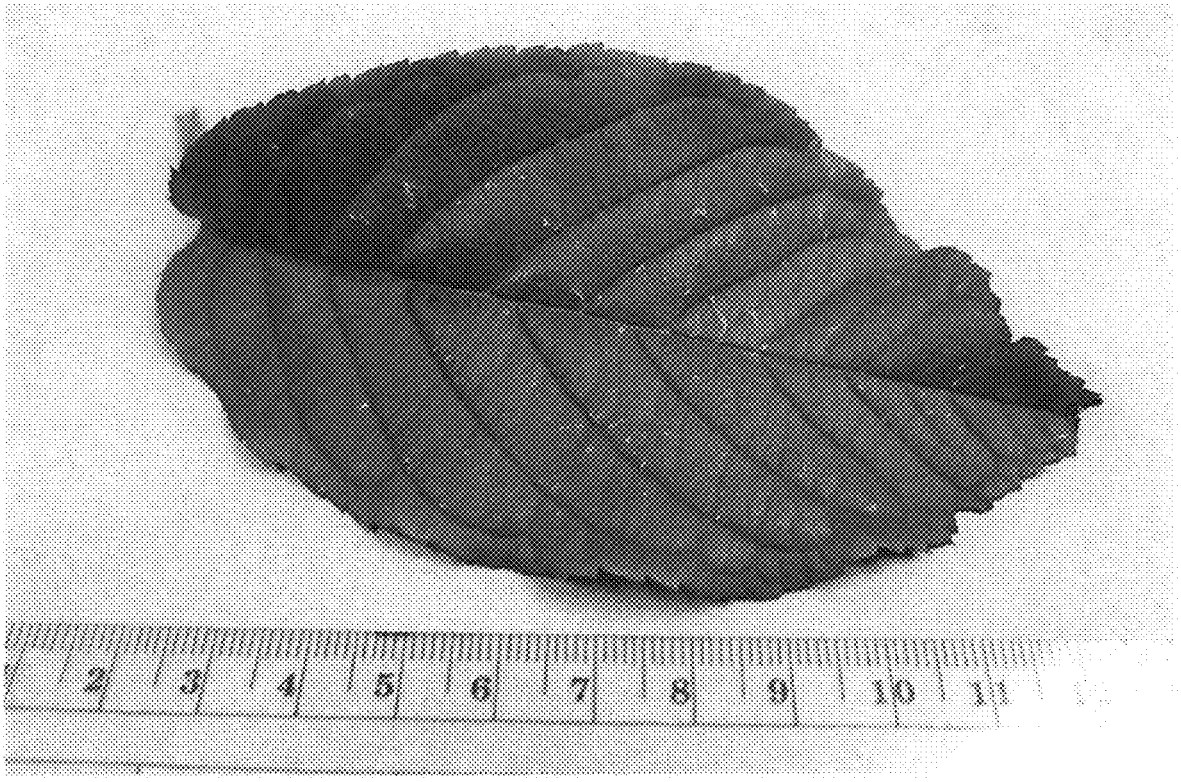
FIG. 10: Shows the typical fall color of a leaf on a display board with a scale.
Figure 11:
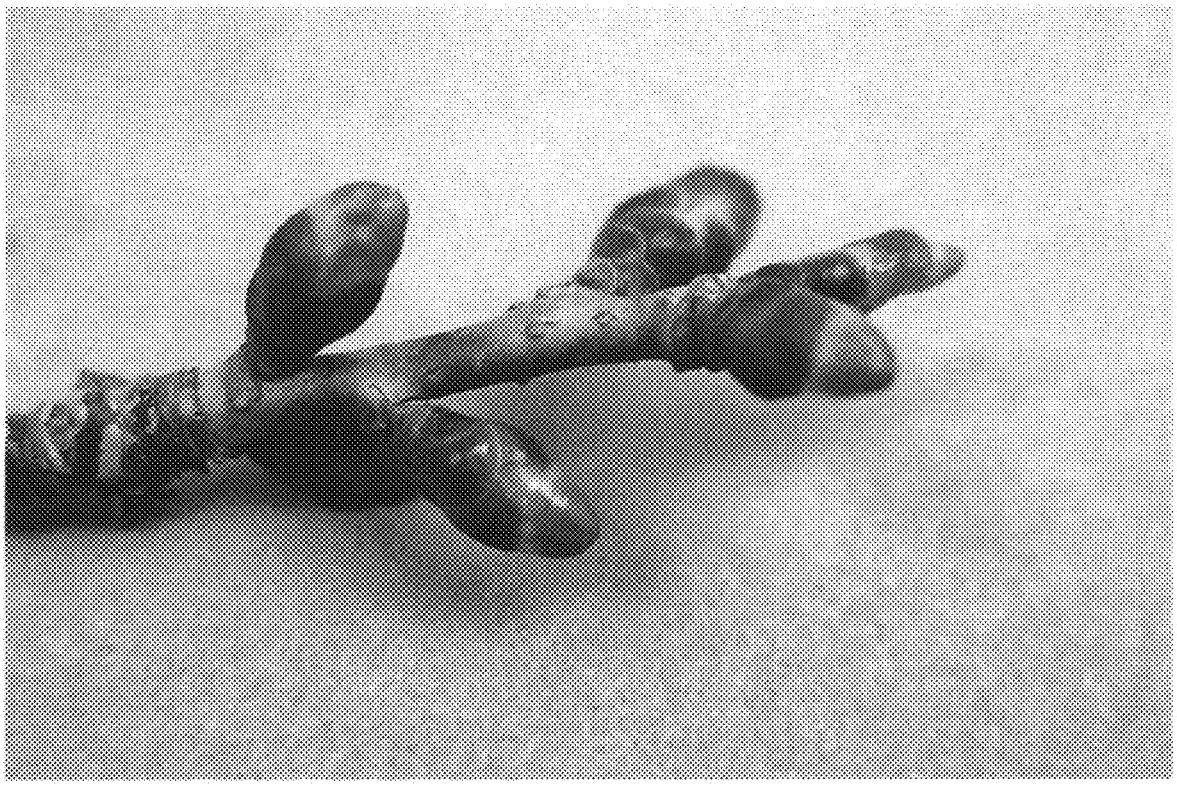
FIG. 11: Shows a winter twig with bud arrangement on a display board.

Scientific name: *Prunus sargentii* 'JFS KW21PS'.

Parentage:

*Seed parent*.—An open pollinated seed grown *Prunus sargentii* designated as '03'.

Tree:

*Overall shape*.—Upright branch orientation. Forming a narrow inverted cone, widest near the top, primary branches are angled at 25 degrees to 35 degrees from the vertical. Height: 7.8 meters at 15 years of age. Width: 3.2 meters at 15 years of age.

*Caliper*.—22.1 cm at 20 cm height above ground and 16.5 cm at 1 meter above ground at 15 years of age. Trunk: Stout, straight.

*Trunk bark texture*.—Smooth with prominent lenticels, becoming somewhat vertically fissured with age.

*Trunk bark color*.—Immature bark color: Greyed Orange 164A to 165B. Mature bark color: Greyed Green198A to Greyed Green 197A showing a mix of both colors. Lenticels: Long oval 10 mm to 20 mm long and 2 mm to 3 mm wide. Horizontal orientation. Greyed Orange 167B. Primary Branches: Stiffly upwards spreading at 25° to 35° from the vertical. Branch color: Greyed Orange 175C.

*Branch lenticels*.—Long oval, Greyed Orange 164C. 1 mm to 2 mm long by 0.5 mm to 1 mm wide.

*Dormant buds*.—Narrow ovoid with imbricate scales. 5 mm to 8 mm long by 2 mm to 3 mm in diameter. Greyed Red 178A to Greyed Purple 184A. Internodes: Average 26 mm on 2 year trees with a range of 15 mm to 32 mm.

*Hardiness*.—Has tolerated field temperatures to 9 degrees F. without damage in Canby, Oreg. This is the minimum temperature this location experienced during the life of the tree. It is believed to have Zone 4 cold hardiness similar to other plants of this species. Disease Resistance: It has shown good resistance to brown rot and shot hole disease.

Leaves: Except as otherwise noted, observations are from twenty vigorous growth leaves.

*Arrangement*.—Alternate.

*Type*.—Simple.

*Texture*.—Smooth.

*Length*.—10 cm to 15 cm, averaging 12 cm on leaves from 2 year old nursery trees.

*Width*.—5.5 cm to 8 cm, averaging 7 cm on leaves from 2 year old nursery trees.

*Petioles*.—1.8 cm to 2.8 cm long, averaging 2.5 cm on leaves from 2 year old nursery trees. Diameter 1.8 mm.

*Overall shape*.—Simple, ovate to oval.

*Margin*.—Sharply serrate.

*Tip*.—Acuminate.

*Base*.—Cordate.

*Stipules*.—15 mm to 20 mm long, 2 mm to 3 mm wide, lanceolate with dissected branching and glandular branch tips.

*Spring leaf color*.—First emerging leaves Yellow Green 144A.

*Summer leaf color*.—Upper leaf surface: Green 136A to Green 139A. Lower leaf surface: Green 138B to Green 138C.

*Bud break averages March 20th in Canby, Oreg. depending on spring weather conditions.*

*Fall leaf color*.—Leaves along the branches first turn Red 53A changing to Red Purple 60A.

*Timing of fall leaf color*.—Average dates for original tree in Boring, Oreg.

*Onset*.—Oct, 24, 2019.

*Peak*.—Nov. 10, 2018, Nov. 15, 2019.

*Latest extent of fall color*.—Nov. 28, 2019.

*Fall color begins and peaks at a time that is typical for the species.*

*Defoliation*.—Complete defoliation averages November 30 in Boring, Oreg.

*Pubescence*.—None.

*Persistence*.—The tree is deciduous.

Flowers:

*Overall*.—Perfect, single flowers with 5 petals. Flowers held in clusters of typically 2 to 5. Round 25 mm to 35 mm across.

*Buds*.—Similar to vegetative buds but broader, 4 mm to 8 mm by 3 mm to 4 mm in diameter.

*Color*.—Unopened buds: Red Purple 64B as the buds swell. Opened flowers: Red Purple 66C to 66D. Petals: Red Purple 66C to 66D to Red Purple 65C. 15 mm to 18 mm long by 7 mm to 10mm wide. Broadly obcordate.

*Sepals*.—Five, acute 8 mm long and 3 mm wide, reflexed, connate at the base forming a tubular hypanthium 8 mm long by 3 mm in diameter.

*Stamen*.—Typically 20 to 25, 8 mm to 12 mm long, centrally clustered surrounding the pistil.

*Anthers*.—Small ovoid, approximately 0.5 mm by 0.2 mm, Yellow Orange 17C.

*Pistil*.—Single. 10 mm to 15 mm long by 0.5 mm-1 mm in diameter. Undivided, with single capitate style. Yellow Green 149A.

*Ovary*.—Superior contained within the base of the hypanthium, ovoid 2 mm high by 1.5 mm in diameter. Green 143D, usually 1.

*Pollen*.—Yellow Orange 17A.

*Pedicel*.—5 cm to 8 cm in length by 1 mm to 2 mm in diameter. Yellow Green 146C.

*Pedicel branches 2 to 5 times with serrulate, lanceolate bracts at the base of each branch. Bracts 6 mm to 10 mm long by 4 mm to 8 mm in diameter. Green 142A.*

*Pubescence*.—None.

*Fragrance*.—Very slight.

*Flowering date in Boring Oreg*.—First boom: Mar. 20, 2019. Peak bloom: Apr. 1, 2019. End bloom: Apr. 12, 2019. Cherry bloom was about 1-2 weeks later than average in 2019.

Fruit: Observations are from a sampling of typical fruit.

*Description*.—A drupe, one seeded. 7 mm to 8 mm long by 5 mm to 6 mm in diameter. Ovoid, glossy, smooth.

*Color*.—Red 45A, as it ripens becoming Greyed Purple 185B.

*Seed*.—A slightly flattened ovoid stone, 5 mm to 7 mm long by 5 mm to 6 mm in diameter. Greyed Orange 164D.

*Fruit production*.—Sparse.

*Usage*.—Wildlife value, taken quickly by birds.

COMPARISON TO OTHER CULTIVATED VARIETIES

Table 1 defines these differences when compared to the most similar commercial cultivars of ornamental cherry.

TABLE 1

| Feature: | *Prunus sargenitii* 'JFS KW21PS' | *Prunus sargentii* 'JFS KW58' (unpatented) | *Prunus sargentii* 'Princeton Snowcloud' U.S. Plant Pat. No. 10,989 |
|---|---|---|---|
| Overall Shape | Narrow Upright - inverted Cone | Upright Oval becoming broader with age. | Broadly Upright |
| Branch Angles | 25-35 degrees | 30-40 degrees | 45 degrees |
| Flowers | Deep Pink: Red Purple 66C to 66D | Light Pink: Red Purple 62B to 62C | Pure White |
| Flowering | Mar. 25 to | Apr. 1-15 | Apr. 8-20 |

TABLE 1-continued

| Feature: | *Prunus sargenitii* 'JFS KW21PS' | *Prunus sargentii* 'JFS KW58' (unpatented) | *Prunus sargentii* 'Princeton Snowcloud' U.S. Plant Pat. No. 10,989 |
|---|---|---|---|
| Date | Apr. 10 Average | Average | Average |
| Flower Size | 25-35 mm | 30-40 mm | 35-40 mm |

COMPARISON TO THE SEED PARENT

In comparison to the seed parent *Prunus sargentii* '03', my new variety has a narrower form and more prolific, brighter, deeper pink flowers produced earlier in the season. The form of the seed parent is broadly vase shaped, while my new variety shaped like an upright, narrow inverted cone. The seed parent produced only moderate numbers of flowers while my new variety flowers prolifically and one to two weeks earlier. The flower color of the seed parent is Red Purple 63C to 63D while the flower color of my new variety is Red Purple 66C to 66D.

I claim:

1. A new and distinct variety of ornamental cherry tree, substantially as herein illustrated and described.

* * * * *